US012752056B2

(12) United States Patent
Bidi et al.

(10) Patent No.: US 12,752,056 B2
(45) Date of Patent: Oct. 6, 2026

(54) MAGNETIC AUTOINJECTOR

(71) Applicant: ARGERON MEDİKAL ARAŞTIRMA SANAYİ VE TİCARET ANONİM ŞİRKETİ, Antalya (TR)

(72) Inventors: Bülent Bidi, Antalya (TR); Abdullah Olgun, Antalya (TR)

( * ) Notice: Subject to any disclaimer, the term of this patent is extended or adjusted under 35 U.S.C. 154(b) by 369 days.

(21) Appl. No.: 18/569,949

(22) PCT Filed: Jun. 20, 2022

(86) PCT No.: PCT/TR2022/050621
§ 371 (c)(1),
(2) Date: Dec. 13, 2023

(87) PCT Pub. No.: WO2022/271133
PCT Pub. Date: Dec. 29, 2022

(65) Prior Publication Data
US 2024/0424213 A1 Dec. 26, 2024

(30) Foreign Application Priority Data
Jun. 22, 2021 (TR) ................................ 2021/010143

(51) Int. Cl.
*A61M 5/20* (2006.01)
*A61M 5/315* (2006.01)
*A61M 5/32* (2006.01)

(52) U.S. Cl.
CPC .......... *A61M 5/20* (2013.01); *A61M 5/31511* (2013.01); *A61M 2005/206* (2013.01); *A61M 5/31501* (2013.01); *A61M 2005/31516* (2013.01); *A61M 2005/31518* (2013.01); *A61M 2005/3223* (2013.01); *A61M 2205/02* (2013.01); *A61M 2205/0272* (2013.01); *A61M 2205/8287* (2013.01)

(58) Field of Classification Search
CPC A61M 5/20; A61M 5/31511; A61M 5/31501; A61M 2005/206; A61M 2005/31516; A61M 2005/31518; A61M 2005/3223; A61M 2205/02; A61M 2205/0272; A61M 2205/8287
See application file for complete search history.

(56) References Cited

U.S. PATENT DOCUMENTS

| | | | | |
|---|---|---|---|---|
| 2011/0077599 | A1 | 3/2011 | Wozencroft | |
| 2013/0310745 | A1 | 11/2013 | Latham | |
| 2017/0304557 | A1* | 10/2017 | Chettiar | A61M 37/0015 |
| 2018/0169337 | A1* | 6/2018 | Paschal | A61M 5/20 |
| 2018/0193564 | A1 | 7/2018 | Dahmani | |

FOREIGN PATENT DOCUMENTS

| | | |
|---|---|---|
| CN | 201044845 Y | 4/2008 |

OTHER PUBLICATIONS

International Search Report and Written Opinion of the International Searching Authority for corresponding PCT/TR2022/050621 dated Sep. 12, 2022.

* cited by examiner

*Primary Examiner* — Tasnim Mehjabin Ahmed
(74) *Attorney, Agent, or Firm* — Egbert, McDaniel & Swartz, PLLC

(57) ABSTRACT

Disclosed is a magnetic autoinjector for first aid and emergency intervention to oneself or others, which is used in cases where intradermal, subcutaneous or intramuscular injection is needed in the living body and provides a safe and easy use.

3 Claims, 1 Drawing Sheet

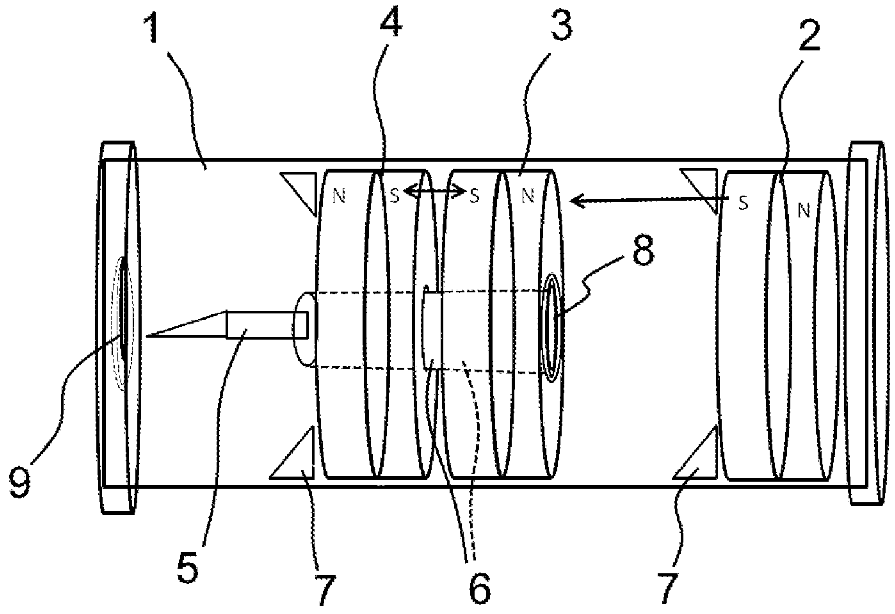
1
4
3
2
N
S
S
N
S
N
8
9
5
7
6
7

MAGNETIC AUTOINJECTOR

TECHNICAL FIELD

The invention generally relates to injectors (syringes) used for injecting drugs into the living body.

In particular, the invention requires first aid and emergency intervention to oneself or others; It is about the magnetic autoinjector, which is used in cases where intradermal, subcutaneous or intramuscular injection is needed in the living body and provides a safe and easy use.

BACKGROUND OF THE ART

Today, injectors are used in cases where it is necessary to inject drugs intradermally, subcutaneously or intramuscularly in the living body. In the most general form, injectors consist of a tube in which the drug to be injected is filled, a needle that allows the drug to be transferred to the living body, and a pushing element that allows the drug to be pushed.

In the current art, injectors have been developed in different designs and working styles according to the needs. One of these injector types is autoinjectors. Autoinjectors are designed to deliver a dose of a particular drug. There are two groups of autoinjectors, with and without needles. The disadvantage of the ones with needle is that they have complex working principles with a standard long injector, a piston rod and a spring. The biggest disadvantage of needleless ones (jet injectors) is that they need a non-disposable special apparatus for application and the risk of infection.

In the state of the art, some documents were found in the research on injectors. The document numbered WO2014162439A1 is about a syringe type injector without a piston, which is easy to carry and aims to inject the drug solution in a simple manner. In this syringe, a pushing structure is formed in its body, which uses the magnetic force to discharge the drug solution. In this structure, a magnet is placed in a fixed holder at the back of the body and another magnet is placed in the inner holder that allows the drug to be injected. Said magnets are positioned inside the fixed holder and the inner holder in such a way that the same poles are facing each other, that is, they are positioned in such a way that the fixed holder and the inner holder repel each other. At the same time, the inner holder is locked by a stopper outside the body. The inner holder, which is released after the movement of the stopper, moves towards the end of the body as a result of the magnets pushing each other, and the drug solution is provided to come out of the body end. In this embodiment, the magnet only provides the discharge of the liquid in the syringe, while the entry of the syringe needle into the skin is provided by the user. At the same time, said injector needle is outside the injector body and is fixed. With this structure, the injector configuration mentioned does not provide a fast, easy and safe use.

Document EP3338833B1 is about an automatic injector. In this document, a pushing mechanism with a spring mechanism is used to throw the liquid drug substance found in the syringe out of the syringe. The drive of this spring mechanism is provided by a mechanical trigger button placed outside the injector. In this embodiment, the piston movement of the injector and the insertion of the needle into the skin are provided by a spring mechanism. The size of the spring mechanism used affects the size of the injector body. In addition, the needle coming out of the injector body remains at the outside. In this state, the mentioned structure cannot go below a certain size, and leaving the needle out is a disadvantage in terms of safety.

As a result, improvements are made regarding injectors, therefore, new structures are needed that will eliminate the disadvantages mentioned above and bring solutions to existing systems.

OBJECTIVE OF THE INVENTION

The present invention relates to a magnetic autoinjector that meets the above-mentioned requirements, eliminates all disadvantages and brings some additional advantages.

The main purpose of the invention is to ensure that a certain dose of the drug is automatically injected intradermally, subcutaneously or intramuscularly in the living body.

An aim of the invention is to ensure that the injection process is carried out automatically with a structure that does not need a piston rod and a spring mechanism. By not using the piston rod and the spring mechanism, it is aimed to introduce an injector that is shorter and smaller than the existing technique.

In order to realize all the advantages mentioned above and which will be understood from the detailed description below, the present invention is a magnetic autoinjector that is used in cases where intradermal, subcutaneous or intramuscular injection is needed in the living body, allowing a certain dose of liquid medication to be injected into the living body easily and safely; so that having a structure containing:

- the injector body, which is in a closed cylindrical form and having an outlet opening at the end,
- stationary magnet, which is positioned in the injector body, mostly in the middle of the injector body, with an inlet opening on it,
- a needle magnet with a needle on it, positioned in the injector body, between the stationary magnet and the outlet opening, close to the stationary magnet and with the same poles facing each other in order to ensure that they apply a repulsive force,
- a piston magnet positioned in the injector body, on the other side of the stationary magnet, with the opposite poles facing each other and with liquid medication between them, in order to ensure that they apply a pulling force to each other,
- The transfer channel located inside the stationary magnet and the needle magnet, which provides the transfer of the liquid drug entering the inlet opening to the needle,
- locking elements that keep the piston magnet and needle magnet stationary against pulling and pushing forces when the injector is not used.

The structural and characteristic features of the invention and all its advantages will be understood more clearly thanks to the figures given below and the detailed description written with reference to these figures. For this reason, the evaluation should be made by taking these figures and detailed explanation into consideration.

BRIEF DESCRIPTION OF THE FIGURES

In order to best understand the embodiment of the present invention and its advantages with additional elements, it should be evaluated together with the figures described below.

FIG. 1 is a general view of the magnetic autoinjector which is the subject of the invention.

REFERENCE NUMBERS

1. Injector body
2. Piston magnet

3. Stationary magnet
4. Needle magnet
5. Needle
6. Transfer channel
7. Locking element
8. Inlet opening
9. Exit opening

DETAILED DESCRIPTION OF THE INVENTION

In this detailed explanation, the preferred embodiments of the magnetic autoinjector subject to the invention are explained only for a better understanding of the subject and without any limiting effect.

The invention is a magnetic autoinjector, which is used in cases where intradermal, subcutaneous or intramuscular injection is needed in the living body, allowing a certain dose of liquid medicine to be injected into the living body easily and safely; that contains;

the injector body (1), which has a closed cylindrical form and has an outlet opening (9) at the end, a stationary magnet (3) with an inlet opening (8) positioned in a stationary manner in the injector body (1), mostly in the middle region of the injector body (1), a needle magnet (4) with a needle (5) on it, positioned in the injector body (1), between the stationary magnet (3) and the outlet opening (9), close to the stationary magnet (3) and with the same poles facing each other to enable them to apply a repulsive force.

a piston magnet (2) located inside the injector body (1), on the other side of the stationary magnet (3), with its opposite poles facing each other and with liquid medicine between them, in order to provide a pulling force to each other, the transfer channel (6), located inside the stationary magnet (3) and the needle magnet (4), which provides the transfer of the liquid medicine entering the inlet opening (8) to the needle (5), locking elements (7) that keep the piston magnet (2) and needle magnet (4) in a stationary manner against pulling and pushing forces when the injector is not in use.

In FIG. 1, there is a general view of the magnetic injector which is the subject of the invention. Said magnetic autoinjector in its most general form consists of an injector body (1), a piston magnet (2) positioned in it, a stationary magnet (3) and a needle magnet (3) to which the needle (5) is connected. The injector body (1) has a cylindrical structure similar to the existing injectors and includes an exit opening (9) at its tip that allows the needle (5) to come out. Piston magnet (2), stationary magnet (3) and needle magnet (4) are positioned respectively on the inside of the injector body (1), again in accordance with the form of the injector body (1). The piston magnet (1) provides pushing the liquid medicine found inside the injector body (1) and between the piston magnet (2) and the stationary magnet (3). The needle magnet (4) carries the needle (5) on it and provides its movement. The stationary magnet (2) is located in the middle of the injector body (1) and provides the movement of the piston magnet (2) and the needle magnet (4). In order to achieve this, the opposite poles of the piston magnet (2) and the stationary magnet (3) face each other, and the same poles of the needle magnet (4) and the stationary magnet (3) face each other. In this state, the stationary magnet (3), while pulling the piston magnet (2) towards itself, pushes the needle magnet (4) and causes the needle (5) to come out of the exit opening (9). At the same time, there is a transfer channel (6) that passes through the stationary magnet (3) and the needle magnet (4) in order to ensure that the liquid drug between the piston magnet (2) and the stationary magnet (3) reaches the needle (5) by pushing. After the liquid drug is pushed, it enters through the inlet opening (8) on the stationary magnet (3) and reaches the needle (5) via the transfer channel (6). Said transfer channel (6) has a flexible and extensible structure in order to ensure the movement of the needle magnet (4) towards the exit opening (9).

There are locking elements (7) inside the injector body (1) to ensure that the piston magnet (2) and the needle magnet (4) remain fixed when the magnetic autoinjector is not in use. Said locking elements (7) lock the piston magnet (2) in the pulling direction, while locking the needle magnet (4) in the pushing direction. In this way, it is ensured that the liquid medicine is not sent to the needle (5) when the injector is not used, and that the needle (5) remains inside the injector body (1).

The Working Mode of the Preferred Embodiment of the Invention is as Follows:

Currently, the piston magnet (2) and the needle magnet (4) are locked with the locking elements (7) in the magnetic autoinjector. There is liquid medicine between the piston magnet (2) and the stationary magnet (3). When the liquid drug is desired to be injected into the living body, firstly the locking elements (7) are triggered and the piston magnet (2) and the needle magnet (4) are released. The released piston magnet (2) is attracted by the stationary magnet (3); the needle magnet (4) is pushed by the stationary magnet (3). During this movement, the liquid medicine between the piston magnet (2) and the stationary magnet (3) enters through the inlet opening (8) on the stationary magnet (3) and moves towards the needle (5) via the transfer channel (6). The needle magnet (4) also moves towards the exit opening (9) with the flexible structure of the transfer channel (6) and it is ensured that the needle (5) exits from the exit opening (9) and reaches the living body. As a result of this movement, the piston magnet (2) touches the stationary magnet (3), and the liquid medicine between them reaches the needle (5) through the transfer channel (6) and is injected into the living body.

After the injection process, the needle (5) is pressed against a hard place and the needle magnet (4) is brought to its initial position. In order to achieve this, the surfaces of the locking elements (7) facing the exit opening (9) are shaped obliquely. The needle magnet (4) opens the locking elements (7) by pushing their oblique surfaces, and when it passes to the upper side of the locking elements (7), locking is achieved again. In this way, it is ensured that the needle (5) stays in the injector body (1) so that it will not puncture again.

The invention claimed is:

1. A magnetic autoinjector that is used in cases where intradermal, subcutaneous or intramuscular injection is needed in the living body, allowing a certain dose of liquid medicine to be injected into the living body easily and safely, the magnetic autoinjector comprising: an injector body which has a closed cylindrical form and has an outlet opening at an end thereof; a stationary magnet positioned in a stationary manner the injector body mostly in a middle region of the injector body, with an inlet opening; a needle magnet with a needle on it that is positioned in the injector body between the stationary magnet and the outlet opening, being closer to the stationary magnet, wherein same poles of the needle magnet and the stationary magnet face each other to enable them to apply a repulsive force; a piston magnet located inside the injector body on the other side of the stationary magnet, wherein opposite poles of the piston magnet and the stationary magnet face each other in order to provide a pulling force to each other and with liquid medicine between them; a transfer channel, located inside the stationary magnet and the needle magnet, which provides the transfer of the liquid medicine entering the inlet opening to the needle; and locking elements that keep the piston magnet and needle magnet fixed against pulling and pushing forces when the injector is not in use.

2. The magnetic autoinjector according to claim 1, wherein the needle magnet contains a flexible or extensible transfer channel that allows it to move away from the stationary magnet to the outlet opening.

3. The magnetic autoinjector in accordance with claim 1, wherein the locking elements whose surfaces face the outlet opening are shaped obliquely, which ensures that when the needle is punctured on a hard surface it remains inside the injector body after the injection process.

* * * * *